(12) United States Patent
Peine et al.

(10) Patent No.: US 9,168,050 B1
(45) Date of Patent: Oct. 27, 2015

(54) END EFFECTOR CONSTRUCTION

(75) Inventors: William J. Peine, Ashland, MA (US);
Andres Chamorro, Waltham, MA (US)

(73) Assignee: Cambridge Endoscopic Devices, Inc., Framingham, MA (US)

( * ) Notice: Subject to any disclaimer, the term of this patent is extended or adjusted under 35 U.S.C. 154(b) by 765 days.

(21) Appl. No.: 13/423,434

(22) Filed: Mar. 19, 2012

Related U.S. Application Data (60) Provisional application No. 61/466,999, filed on Mar. 24, 2011, provisional application No. 61/482,397, filed on May 4, 2011.

(51) Int. Cl.
*A61B 17/00* (2006.01)
*A61B 17/28* (2006.01)

(52) U.S. Cl.
CPC .................. *A61B 17/2816* (2013.01)

(58) Field of Classification Search
CPC .... A61B 17/29; A61B 17/28; A61B 17/2804; A61B 17/2812; A61B 17/2816; A61B 2017/2926; A61B 2017/2947
USPC .................................................. 606/205–210
See application file for complete search history.

(56) References Cited

U.S. PATENT DOCUMENTS

| | | |
|---|---|---|
| 2,028,635 A | 1/1936 | Wappler |
| 2,507,710 A | 5/1950 | Grosso |
| 2,790,437 A | 4/1957 | Moore |
| 3,510,923 A * | 5/1970 | Blake ............................ 606/158 |
| 3,557,780 A | 1/1971 | Sato |
| 3,858,577 A | 1/1975 | Bass et al. |
| 3,895,636 A | 7/1975 | Schmidt |
| 4,483,562 A | 11/1984 | Schoolman |
| 4,644,651 A * | 2/1987 | Jacobsen ......................... 30/251 |
| 4,688,554 A | 8/1987 | Habib |
| 4,728,020 A | 3/1988 | Green et al. |
| 4,763,669 A | 8/1988 | Jaeger |
| 4,872,456 A | 10/1989 | Hasson |
| 4,880,015 A | 11/1989 | Nierman |
| 4,944,093 A | 7/1990 | Falk |
| 4,944,741 A | 7/1990 | Hasson |
| 4,945,920 A | 8/1990 | Clossick |
| 5,002,543 A | 3/1991 | Bradshaw et al. |

(Continued)

FOREIGN PATENT DOCUMENTS

| | | |
|---|---|---|
| EP | 0 095 970 A2 | 12/1983 |
| EP | 0 448 284 A2 | 9/1991 |

(Continued)

OTHER PUBLICATIONS

Nakamura et al., "Multi-DOF Forceps Manipulator System for Laparoscopic Surgery"—5 pgs.

(Continued)

*Primary Examiner* — Katrina Stransky
(74) *Attorney, Agent, or Firm* — David M. Driscoll, Esq.

(57) ABSTRACT

A medical instrument tool or end effector constructed of a fixed jaw having a distal grasping end and a proximal body end; a movable jaw having a distal grasping end and a proximal body end; a slide member controlled from a tool actuator, adapted for linear translation and supported between the jaws; at least one link that inter-couples between the slide member and the movable jaw; and a pivot member mounted at the fixed jaw and for engagement with a slot in the body end of the movable jaw.

22 Claims, 12 Drawing Sheets

(56) References Cited

U.S. PATENT DOCUMENTS

| | | | |
|---|---|---|---|
| 5,042,707 A | 8/1991 | Taheri | |
| 5,209,747 A | 5/1993 | Knoepfler | |
| 5,251,611 A | 10/1993 | Zehel et al. | |
| 5,271,381 A | 12/1993 | Ailinger et al. | |
| 5,273,026 A | 12/1993 | Wilk | |
| 5,275,608 A | 1/1994 | Forman et al. | |
| 5,286,255 A * | 2/1994 | Weber | 604/22 |
| 5,314,424 A | 5/1994 | Nicholas | |
| 5,330,502 A | 7/1994 | Hassler et al. | |
| 5,344,428 A | 9/1994 | Griffiths | |
| 5,383,880 A | 1/1995 | Hooven | |
| 5,386,818 A | 2/1995 | Schneebaum et al. | |
| 5,395,367 A | 3/1995 | Wilk | |
| 5,405,344 A | 4/1995 | Williamson et al. | |
| 5,433,721 A | 7/1995 | Hooven et al. | |
| 5,441,494 A | 8/1995 | Ortiz | |
| 5,454,827 A | 10/1995 | Aust et al. | |
| 5,501,654 A | 3/1996 | Failla et al. | |
| 5,520,678 A | 5/1996 | Heckele et al. | |
| 5,599,151 A | 2/1997 | Daum et al. | |
| 5,618,294 A | 4/1997 | Aust et al. | |
| 5,643,294 A | 7/1997 | Tovey et al. | |
| 5,702,408 A | 12/1997 | Wales et al. | |
| 5,759,151 A | 6/1998 | Sturges | |
| 5,766,196 A | 6/1998 | Griffiths | |
| 5,772,578 A | 6/1998 | Heimberger et al. | |
| 5,823,066 A | 10/1998 | Huitema et al. | |
| 5,827,177 A | 10/1998 | Oneda et al. | |
| 5,851,208 A | 12/1998 | Trott | |
| 5,855,569 A | 1/1999 | Komi | |
| 5,873,817 A | 2/1999 | Kokish et al. | |
| 5,899,425 A | 5/1999 | Corey, Jr. et al. | |
| 5,899,914 A | 5/1999 | Zirps et al. | |
| 5,904,647 A | 5/1999 | Ouchi | |
| 5,916,146 A | 6/1999 | Allotta et al. | |
| 5,916,147 A | 6/1999 | Boury | |
| 5,921,956 A | 7/1999 | Grinberg et al. | |
| 5,928,263 A | 7/1999 | Hoogeboom | |
| 5,938,678 A | 8/1999 | Zirps et al. | |
| 5,944,713 A | 8/1999 | Schuman | |
| 5,947,996 A * | 9/1999 | Logeman | 606/205 |
| 6,126,633 A | 10/2000 | Kaji et al. | |
| 6,174,280 B1 | 1/2001 | Oneda et al. | |
| 6,210,377 B1 | 4/2001 | Ouchi | |
| 6,210,378 B1 | 4/2001 | Ouchi | |
| 6,270,453 B1 | 8/2001 | Sakai | |
| 6,551,238 B2 | 4/2003 | Staud | |
| 6,623,424 B2 | 9/2003 | Hayakawa et al. | |
| 6,638,214 B2 | 10/2003 | Akiba | |
| 6,656,195 B2 | 12/2003 | Peters et al. | |
| 6,666,854 B1 | 12/2003 | Lange | |
| 6,752,756 B2 | 6/2004 | Lunsford et al. | |
| 6,761,717 B2 | 7/2004 | Bales et al. | |
| 7,090,637 B2 | 8/2006 | Danitz et al. | |
| 7,147,650 B2 | 12/2006 | Lee | |
| 8,568,443 B1 * | 10/2013 | Jackman et al. | 606/205 |
| 2002/0045803 A1 | 4/2002 | Abe et al. | |
| 2002/0095175 A1 | 7/2002 | Brock et al. | |
| 2002/0133173 A1 | 9/2002 | Brock et al. | |
| 2002/0156497 A1 | 10/2002 | Nagase et al. | |
| 2002/0177750 A1 | 11/2002 | Pilvisto | |
| 2002/0177847 A1 | 11/2002 | Long | |
| 2003/0065359 A1 | 4/2003 | Weller et al. | |
| 2003/0109898 A1 | 6/2003 | Schwarz et al. | |
| 2003/0135204 A1 | 7/2003 | Lee et al. | |
| 2003/0149338 A1 | 8/2003 | Francois et al. | |
| 2003/0216618 A1 | 11/2003 | Arai | |
| 2004/0049205 A1 | 3/2004 | Lee et al. | |
| 2004/0111009 A1 | 6/2004 | Adams et al. | |
| 2004/0138529 A1 | 7/2004 | Wiltshire et al. | |
| 2004/0176751 A1 | 9/2004 | Weitzner et al. | |
| 2004/0193146 A1 | 9/2004 | Lee et al. | |
| 2004/0236316 A1 | 11/2004 | Danitz et al. | |
| 2005/0049580 A1 | 3/2005 | Brock et al. | |
| 2005/0107667 A1 | 5/2005 | Danitz et al. | |
| 2005/0165429 A1 * | 7/2005 | Douglas et al. | 606/157 |
| 2005/0228440 A1 | 10/2005 | Brock et al. | |
| 2005/0251112 A1 | 11/2005 | Danitz et al. | |
| 2005/0273084 A1 | 12/2005 | Hinman et al. | |
| 2005/0273085 A1 | 12/2005 | Hinman et al. | |
| 2006/0020287 A1 * | 1/2006 | Lee et al. | 606/205 |
| 2006/0195097 A1 | 8/2006 | Evans et al. | |
| 2006/0206101 A1 | 9/2006 | Lee | |
| 2006/0270909 A1 | 11/2006 | Davis et al. | |
| 2007/0250110 A1 | 10/2007 | Lu et al. | |
| 2009/0018573 A1 * | 1/2009 | Teichtmann | 606/207 |
| 2010/0179540 A1 * | 7/2010 | Marczyk et al. | 606/41 |
| 2010/0217286 A1 * | 8/2010 | Gerber et al. | 606/148 |
| 2010/0298864 A1 * | 11/2010 | Castro | 606/205 |
| 2011/0121050 A1 * | 5/2011 | Nicholas et al. | 227/175.1 |
| 2011/0230910 A1 * | 9/2011 | Stopek et al. | 606/205 |
| 2012/0022584 A1 * | 1/2012 | Donnigan et al. | 606/206 |

FOREIGN PATENT DOCUMENTS

| | | |
|---|---|---|
| EP | 0 626 604 A2 | 5/1994 |
| EP | 0 427 949 B1 | 6/1994 |
| GB | 2 143 920 | 2/1985 |
| WO | 90/05491 | 5/1990 |
| WO | 92/01414 | 2/1992 |
| WO | 94/17965 | 8/1994 |

OTHER PUBLICATIONS

Nakamura, Ryoichi et al., "Multi-DOF Forceps Manipulator System for Laparoscopic Surgery—Mechanism Miniaturized & Evaluation of New Interface," Proc of Fourth International Conference on Medical Image Computing and Computer Assisted Interventions (MICCAI2001), Utrecht, the Netherlands, Oct. 14-17, 2001:pp. 606-613 (2001).

Nakamura, Ryoichi et al., "Development of Forceps Manipulator System for Laparoscopic Surgery," 6 pgs.

Yamashita, Hiromasa et al., "Multi-Slider Linkage Mechanism for Endoscopic Forceps Manipulator," In Proc. of the 2003 IEEE/RSJ, Intl. Conference on Intelligent Robots and Systems, vol. 3, pp. 2577-2582, Las Vegas, Nevada, Oct. 2003.

* cited by examiner

END EFFECTOR CONSTRUCTION

RELATED CASES

Priority for this application is hereby claimed under 35 U.S.C. §119(e) to commonly owned and U.S. Provisional Patent Application Nos. 61/466,999 which was filed on Mar. 24, 2011 and 61/482,397 which was filed on May 4, 2011 each of which were filed in the name of William J. Peine and Andres Chamorro, and each of which is incorporated by reference herein in its entirety.

FIELD OF THE INVENTION

The present invention relates to an end effector or tool construction that is used with a surgical instrument. More particularly, the present invention relates to an improved end effector construction that enables the end effector jaws to close in a more parallel manner.

BACKGROUND OF THE INVENTION

An end effector that employs a multiple bar linkage is known. One reason for using a structure of this type is to enable the jaws of the end effector to be closed in a more parallel manner. However, present end effectors of this type are not effective in providing a uniform grasping action as there is excessive lateral action upon closing the end effector. With existing jaw constructions the jaws travel, upon closing, to provide a significant undesired sheering action where the end effector jaws engage tissue or a vessel.

A rudimentary form of a grasper may be considered as consisting of a pair of jaws with a single pivot point and act like a pair of needle nose pliers. This type of closing action puts immense pressure on tissue portions nearest the apex of the jaws with a squeezing action forcing soft tissue outwards towards the ends of the jaws. This type of end effector can cause severe damage to delicate soft tissue.

An alternative style of jaws is a parallel jaws mechanism such as shown in FIGS. 2-7. This type of jaw mechanism exerts a more even top to bottom clamping pressure on soft tissue but still has a disadvantage in that the top, moveable jaw has a horizontal travel component that can effect a tearing action on soft tissue such as veins as the jaws are closed upon them. The end effector construction shown in FIGS. 2-7 herein employs a multiple bar linkage for operating the end effector.

Figures 2, 3:
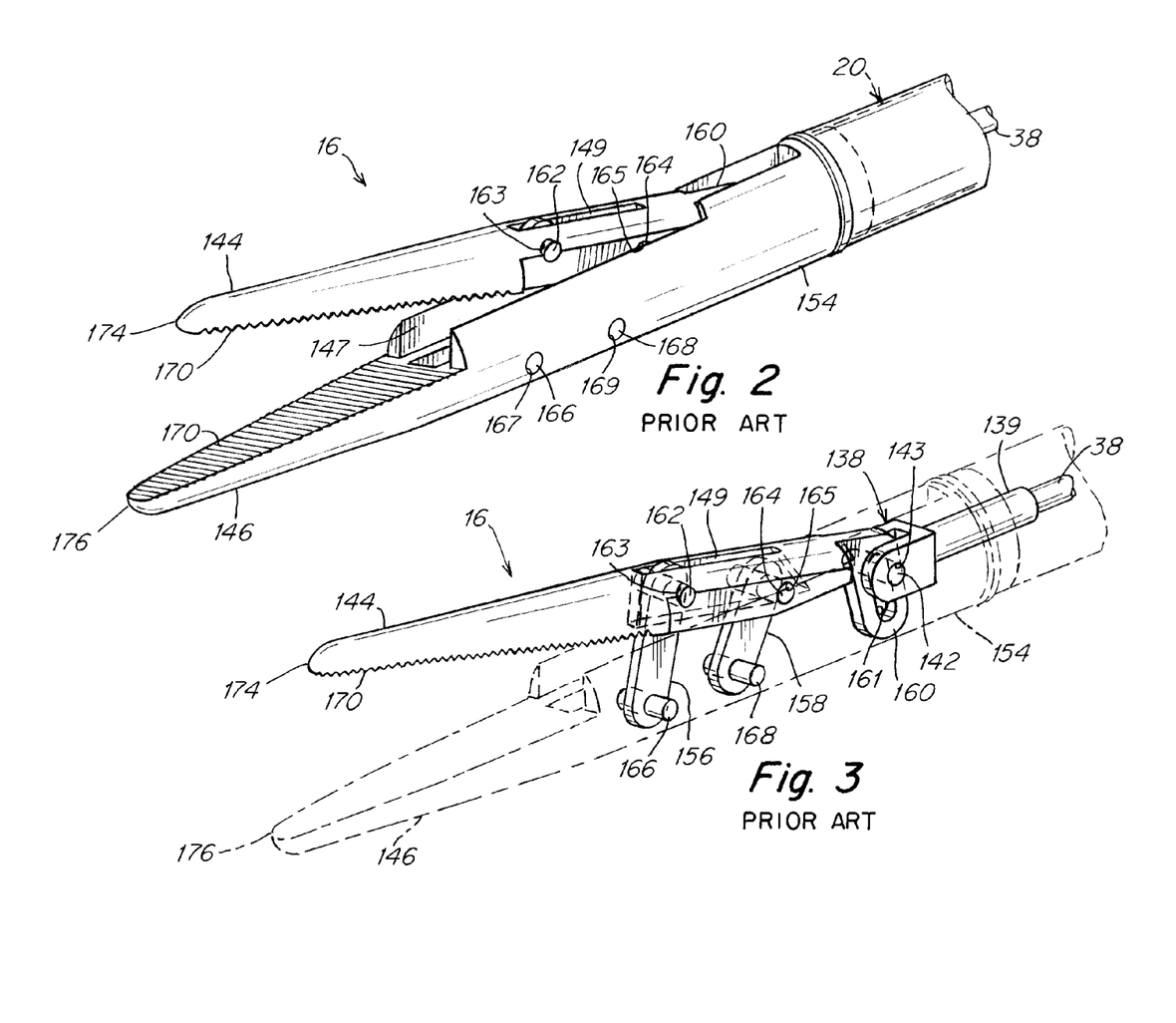
FIG. 2 is an enlarged perspective view of an existing parallel jaws end effector by itself.
FIG. 3 is an enlarged perspective view of the parallel jaws end effector of FIG. 2 but with some portions shown in phantom for clarity.
Figure 4:
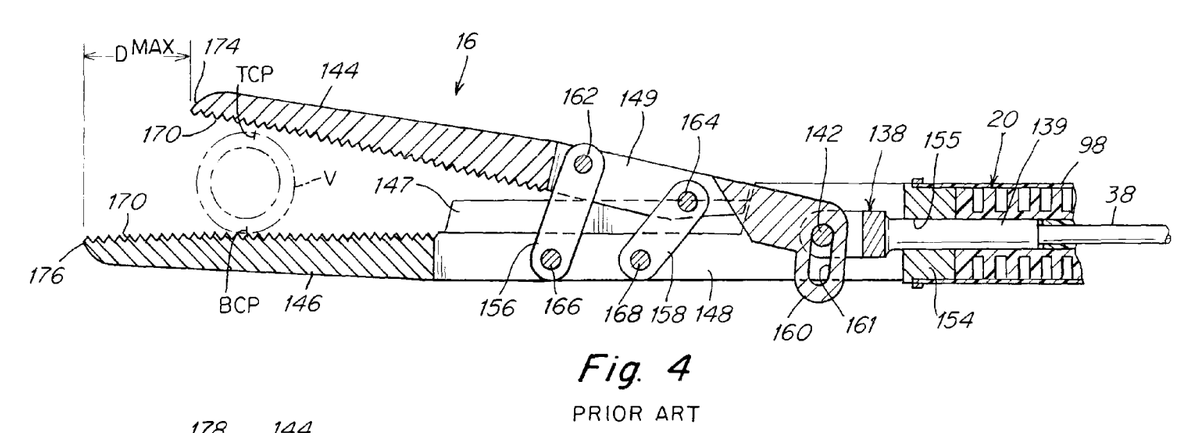
FIGS. 4-7 are schematic cross-sectional views of the parallel jaws in a sequence of positions from fully open to completely closed.

Reference is now made to FIGS. 2-4, which illustrates the fixed jaw 146 and related movable jaw 144. The end effector 16 includes a main body portion 154 of the fixed jaw 146 that is affixed to the distal end of distal bending member 20. A protective sheath 98 may be disposed about the distal bendable member 20 to prevents bodily fluids from entering cavities in the distal bending member. A channel 147 is formed in the main body 154 for receiving the moveable jaw 144 therein. The moveable jaw 144 is hinged to the main body 154 by means of two links 156 and 158 which are attached to fixed pivot points on both the moveable and fixed jaws. As illustrated in FIGS. 2 and 3, the upper ends of links 156, 158 extend into slot 149 formed in the moveable jaw 144 and are joined by pivot pins 162, 164 to bores 163, 165 in the jaw 144. The lower ends of links 156,158 extend into slot 148 formed at the bottom of channel 147 and are joined by pivot pins 166,168 to bores 167,169 in the main body 154. This fixed point linkage arrangement results in significant lateral action as the upper jaw 144 rocks back and forth on links 156 and 158 as can be seen in the sequence views described in FIGS. 4-7.

The actuation cable 38 is attached at its' proximal end to a slider/ratchet mechanism (not shown) in the handle of a surgical tool that, instead of imparting a proximal pulling motion to cable 38 when the jaw actuation lever is squeezed, imparts a distal pushing motion to cable 38 when the jaw actuation lever is squeezed. The distal end of cable 38 is fixed to yoke 138 which is slidably mounted in the main body 154. The yoke has tubular boss 139 which rides in guide/bore 155 in the main body 154. The boss 139 is firmly fixed on the end of cable 38 and is free to slide proximally/distally in the bore 155. The yoke 138 is coupled with an arm extension 160 at the proximal end of moveable jaw 144 by pin 142. The extension arm 160 is disposed angularly to the main longitudinal axis of the movable jaw 144. See, for example, FIGS. 3-5 where the extension arm 160 has an elongated slot 161. The pin 142 is force fit in bores 143 in the yoke 138 and passes through, and is free to slide vertically in, the slot 161 in the extension arm 160. The extension arm 160 thus is free to slide vertically in relation to the yoke 138 so as to accommodate the vertical movements of the moveable jaw as it opens and closes in response to the push/pull action of the cable 38. The jaws 144, 146 have opposing serrations 170 for enhanced the gripping of tissue.

Figure 5:
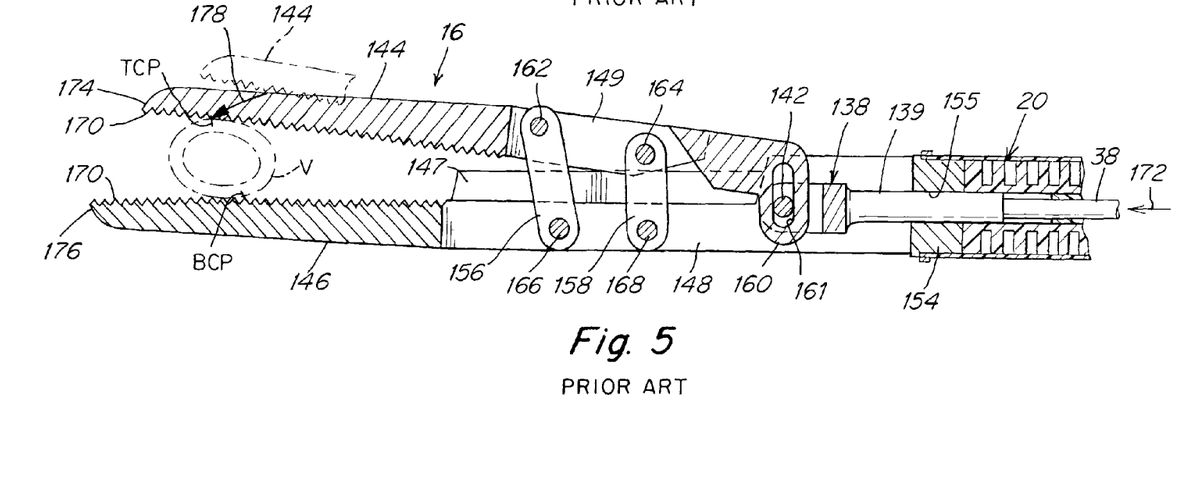
Figure 6:
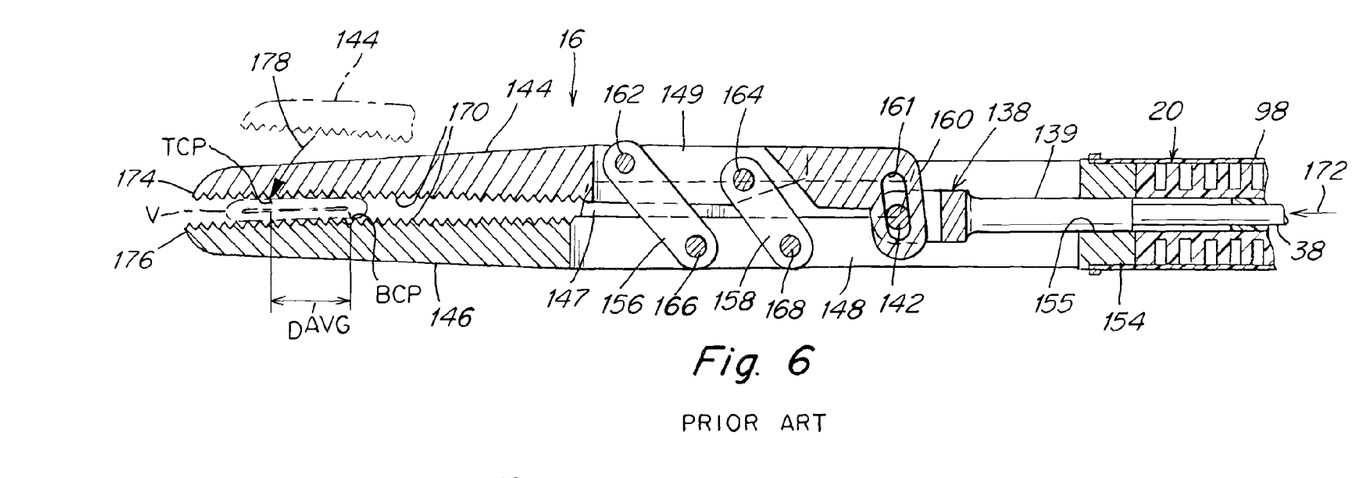
Figure 7:
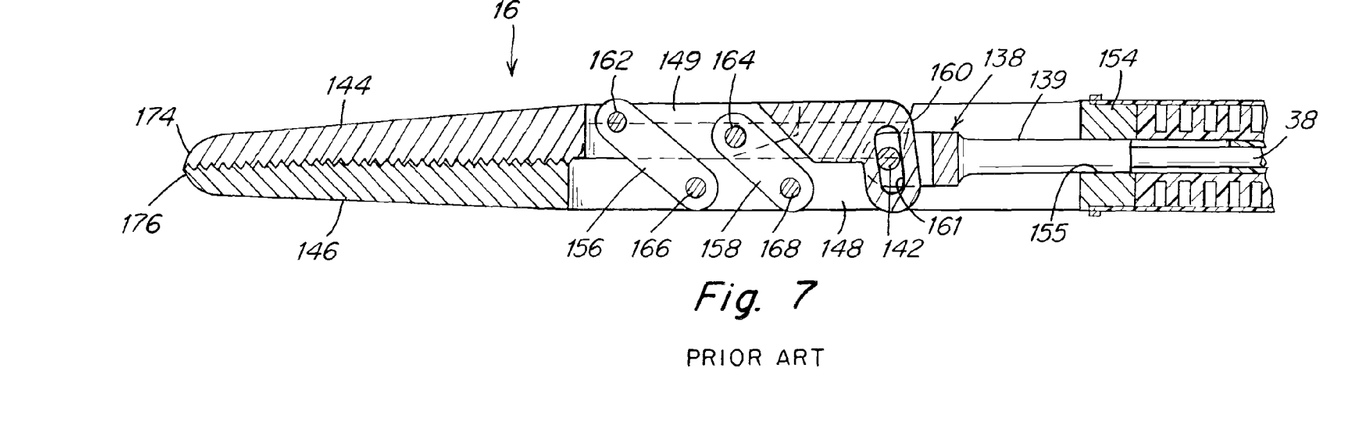

FIGS. 4-7 show a sequence of action as the jaws clamp down on an object such as a the illustrated vein V. FIG. 4 shows the moveable jaw 144 in a fully open position about to close down on the vein V. In this position the tip 174 of the movable jaw 144 is situated a maximum distance $D_{MAX}$ proximally from the tip 176 of the fixed jaw 146. As the jaw actuation lever (not shown) is squeezed, the cable 38 is urged distally (arrow 172) and the serrations 170 on jaw 144 make contact with a top contact point TCP on vein V while the serrations 170 on jaw 146 make contact with bottom contact point BCP on vein V as shown in FIG. 5. As the moveable jaw 144 closes down upon the vein (arrow 178) a rolling action is imparted to the vein V as indicated by the vector of arrow 178. By the time the jaws have closed to the extent illustrated in FIG. 6 the top contact point TCP has traveled an average distance DAVG in relation to the bottom contact point BCP. This rolling motion in conjunction with the serrations 170 can cause a significant tearing action in any soft tissue and is a major drawback to this type of jaw actuation mechanism. The distance DAVG may be slightly less than DMAX due to the offset of TCP and BCP according to how far distal or proximal they occur along the length of the jaw serrations in relation to the size of the tissue grabbed. FIG. 7 shows the jaws fully closed without any tissue present.

Accordingly, it is an object of the present invention to provide an improved end effector construction, and in particular one that has the jaws of the end effector close without any substantial lateral motion between the jaws.

Another object of the present invention is to provide an improved end effector construction with absolute minimum lateral motion between the jaws, and with a structure that is relatively simple, operates effectively and can be manufactured relatively inexpensively.

DETAILED DESCRIPTION

Figure 1:
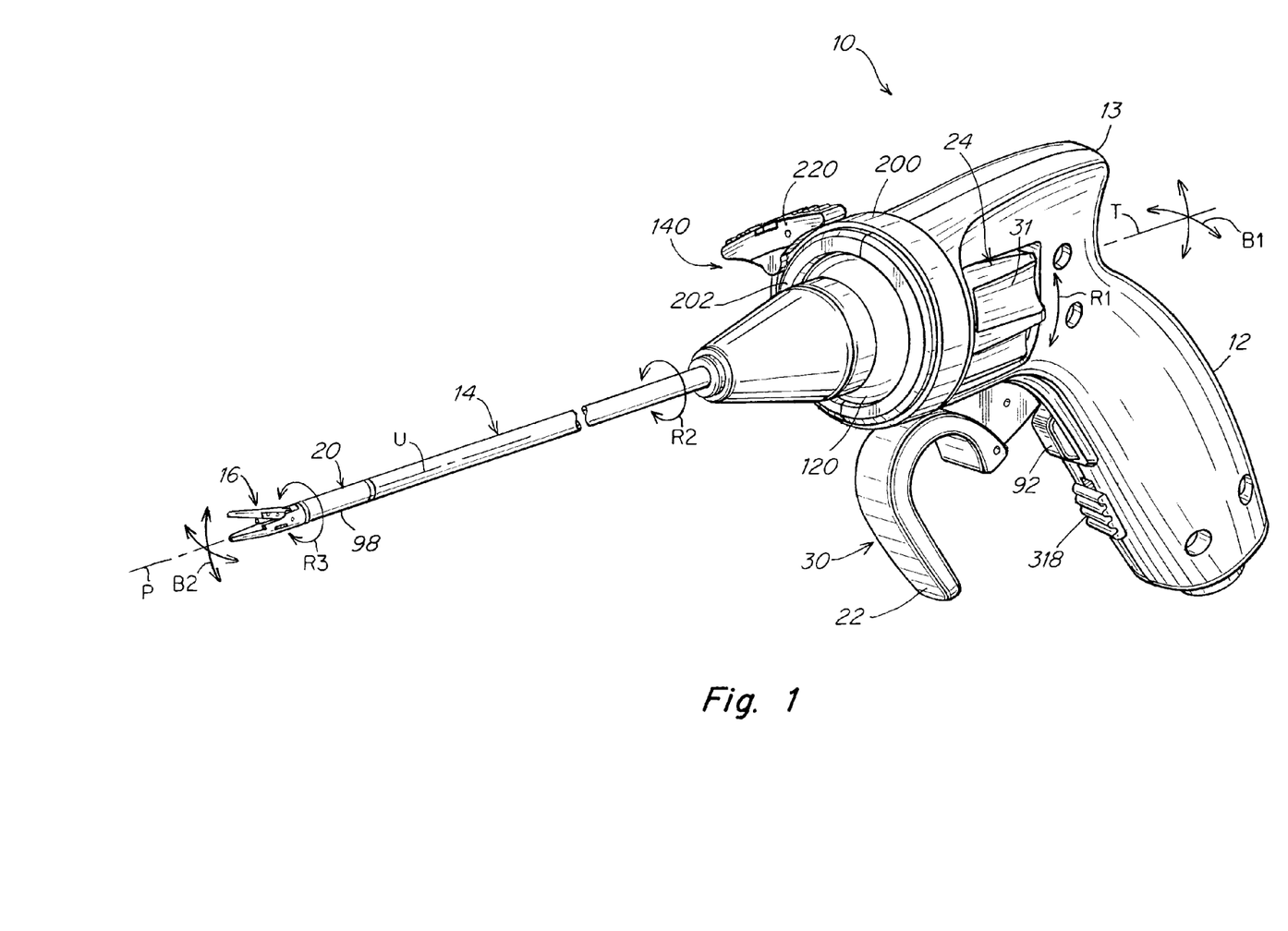
FIG. 1 is a perspective view of a parallel jaws end effector of the invention as used on a surgical instrument such as a laparoscopic instrument.

FIG. 1 shows a parallel jaws end effector mechanism of the present invention as used on a surgical instrument, such as the instrument described in previously filed and co-pending application Ser. No. 12/661,765 filed on Mar. 3, 2010, and hereby incorporated by reference herein in its entirety. Endoscopic instruments such as the instrument shown in FIG. 1 are used in a variety of procedures requiring a variety of end effector tools, one of which may be a grasper to manipulate, position or hold delicate body parts such as tissue, veins, etc. during various surgical procedures. The improved parallel jaws mechanism of the present invention effects an absolute minimal horizontal travel component which practically eliminates any lateral tearing action whatsoever as will be describe in greater detail below.

With reference to FIG. 1 there is illustrated a medical instrument 10 that is basically comprised of a handle 12, proximal bendable member (not shown), instrument shaft 14, distal bendable member 20 and tool or end effector 16. The shaft 14 may be considered as having a longitudinal axis U. Similarly, the handle 12 may be considered as having a longitudinal axis T, and the end effector 16 may be considered as having a distal tip axis P. In FIG. 1 all of the axes U, T and P are in-line. A bending of the handle 12 with respect to the shaft 14 is shown in FIG. 1 by virtue of the double arrows that show an angle B1. This bending at the proximal bendable member causes a corresponding bending at the distal bendable member, via bend control cables (not shown in FIG. 1), resulting in a bend indicated by the double arrows at an angle B2 between the instrument shaft 14 and end effector 16. When the handle is bent downwardly, the end effector bends upwardly. The ratio of bending angle is determined by the ratio of the diameters of the proximal bending member and the distal bending member 20, which, in turn, determines the distance each cable is actuated.

With further reference to FIG. 1, there are illustrated several different instrument motions indicated by rotational arrows. Rotation arrow R1 represents the rotation of the rotation knob 24 about handle axis T. This action, in turn, causes a rotation illustrated by rotation arrow R2 of the shaft about axis U. The rotation knob 24 supports the proximal bendable member 18 which, in turn, supports the instrument shaft 14. The rotation R2 is transmitted to rotation R3 of the end effector 16 about axis P by way of the distal bendable member 20. The actuation cables are anchored at one end at end effector 16 and at the opposite end at the rotation knob 24. The cables control, in a push and pull manner, the end effector 16 as it is rotated to keep axis P at its' preset angle that is fixed by the angle locking means 140. The distal bendable member 20 is generally smaller in diameter than the proximal bendable member and has discs, ribs and slots such as described in the aforementioned Ser. No. 12/661,765. The distal bendable member 20 also preferably has a sheath 98 encasing it to prevent bodily fluids from infiltration.

The surgical instrument of FIG. 1 has a pistol grip style handle 12 with a horn 13 to nestle in the grip of the hand of the surgeon. The shaft portion 14 is inserted through a cannula or port of entry device (not shown) in a patients abdomen and the end effector 16 can be observed with an endoscopic camera and manipulated within the distended abdomen of a patient by using the cannula or port of entry device as a fulcrum for bending action B1, B2 of the handle and end effector. Angle locking mechanism 140 uses an over center lock/release lever 220 to clamp or release the ball 120 in the hub 202 by means of the cinch ring 200. Locking in the angle of the end effector tool axis P with regard to the shaft axis U frees up the surgeons motions to further manipulate the end effector.

A rolling motion can be carried out with the instrument of the present invention. This can occur by virtue of the rotation of the rotation knob 24 relative to the handle 12 about a longitudinal shaft axis. This is represented in FIG. 1 by the rotation arrow R1. When the rotation knob 24 is rotated, in either direction, this causes a corresponding rotation of the instrument shaft 14. This is depicted in FIG. 1 by the rotational arrow R2. This same motion also causes a rotation of the distal bendable member and end effector 16 about an axis that corresponds to the instrument tip, depicted in FIG. 1 as about the longitudinal tip or tool axis P. In FIG. 1 refer to the rotational arrow R3 at the tip of the instrument.

Any rotation of the rotation knob 24, using the finger indents 31, while the instrument is locked (or unlocked) maintains the instrument tip at the same angular position, but rotates the orientation of the tip (tool). For a further explanation of the tip rotational feature refer to co-pending application Ser. No. 11/302,654, filed on Dec. 14, 2005, particularly FIGS. 25-28, which is hereby incorporated by reference in its entirety.

By pushing the handle 12 further into the cannula or port of entry the surgeon can then place the open jaws in position to close about the target object. The surgeon can then use the jaw clamping means 30 to close the jaws on the target object by squeezing the jaw actuation lever 22. This squeezing action is translated into a proximal pulling motion of the push/pull cable 38 through a slider mechanism (not shown). A ratcheting action is normally incorporated into the clamping means 30 to hold jaw clamping pressure when the actuation lever 22 is released. A release button 92 is used to release the clamping pressure and a return spring in the slider returns the jaws to a fully open position. A ratchet disengage slide button 318 may also be incorporated into the handle to disable the ratcheting action if so desired.

Reference is now made to FIGS. 8-14 for an illustration of a first embodiment of the improved parallel jaw mechanism of the present invention. A second embodiment of the instrument is illustrated in FIGS. 15-21. The first embodiment uses a pulling action for jaw closure while the second embodiment uses a pushing action for jaw closure. The first embodiment is first described.

Figure 10:
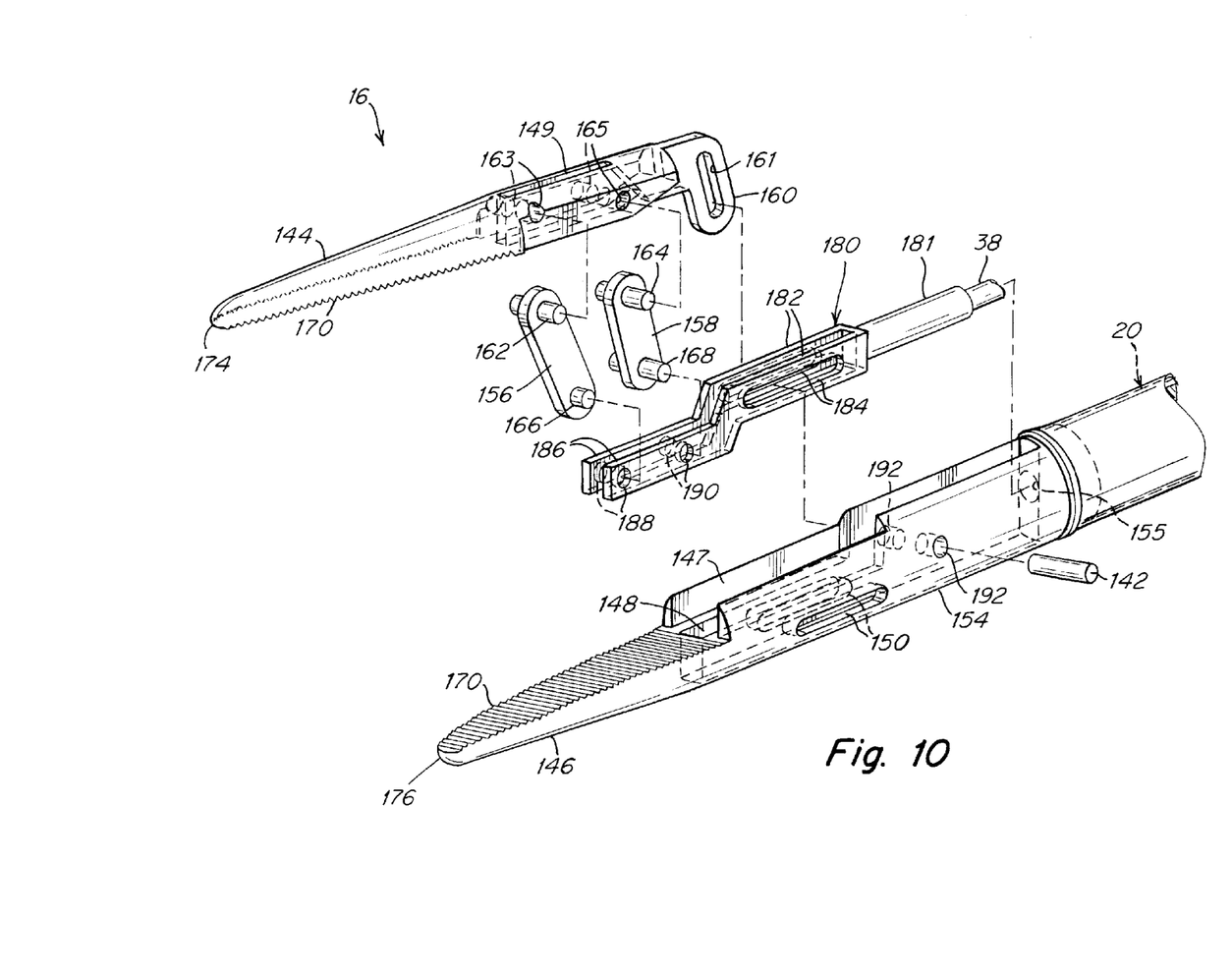
FIG. 10 is an exploded perspective view of the end effector of FIG. 8.

In FIGS. 8-14 the same reference numbers are used where applicable, as previously identified in the instrument shown in FIGS. 2-7, such as the distal bendable member 20, the tool actuation cable 38, links 156, 158 and pivots 162, 164, 166 and 168. Instead of fixed pivot points for the lower ends of links 156, 158 (pins 166, 168 in FIG. 2 fixed with the lower jaw 146) the end effector construction of the present invention utilizes sliding pivot locations by means of the lower ends of the links 156, 158 being supported for translation by engagement with the yoke 180. The yoke 180 essentially functions as a slide member controlled from the actuation cable 38. The yoke 180 includes a boss 181 having extending therefrom elongated arms that each include upper arms 182 and lower arms 186 that are interconnected by an angled transition section. The pins 166, 168 are received in respective bores 188, 190 formed in the lower arms 186 of the yoke 180. As illustrated in FIG. 10, the arms 182 and 186 each include a pair of parallel spaced apart arms, with the lower arms 186 each have the respective aligned bores 188, 190.

Figure 12:
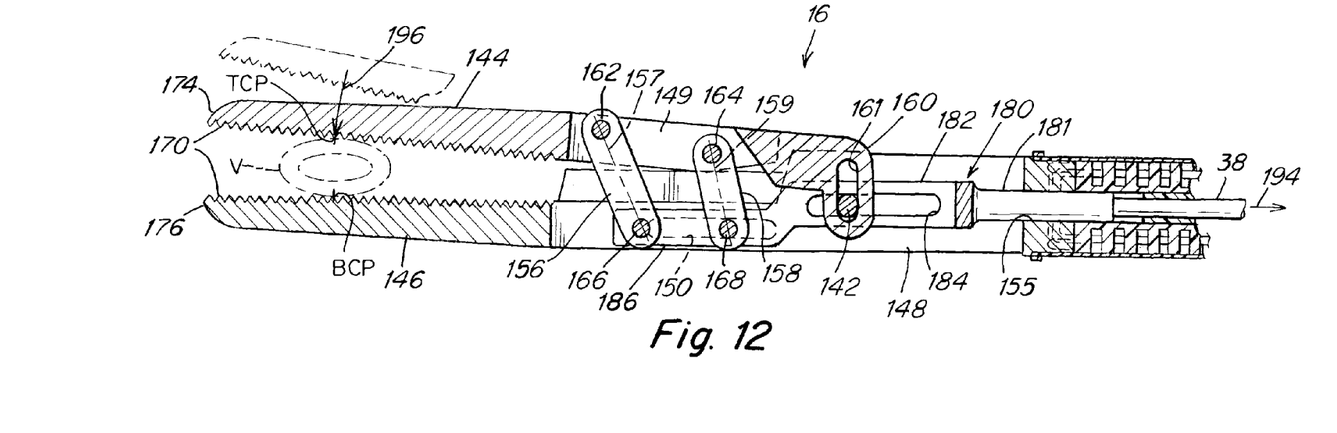

The yoke 180 travels proximally when the cable 38 is pulled (arrow 194 in FIG. 12) to move the end effector jaws toward a closed position. It is to be noted that, while in the prior art embodiment described herein in FIGS. 2-7, the actuation cable 38 is pushed distally (see arrow 172 in FIGS. 5 and 6), in the present invention, in the first embodiment described herein, the actuation cable 38 is pulled proximally (see arrows 194 in FIGS. 12 and 13). The closing action involves having the pin 142 ride in the slot 161 of the extension arm 160 for controlling the action of the movable jaw 144. The extension arm 160 is somewhat elongated, as is the slot 161, and the extension 160 is integral with and extends substantially orthogonal to the length of the movable jaw 144 and the length of the upper arms 182 such as shown in FIG. 12. The action between the cable 38, yoke 180, pin 142 and movable jaw 144 causes a substantially parallel closing as illustrated by the arrow 196 in FIG. 12.

Figures 8, 9:
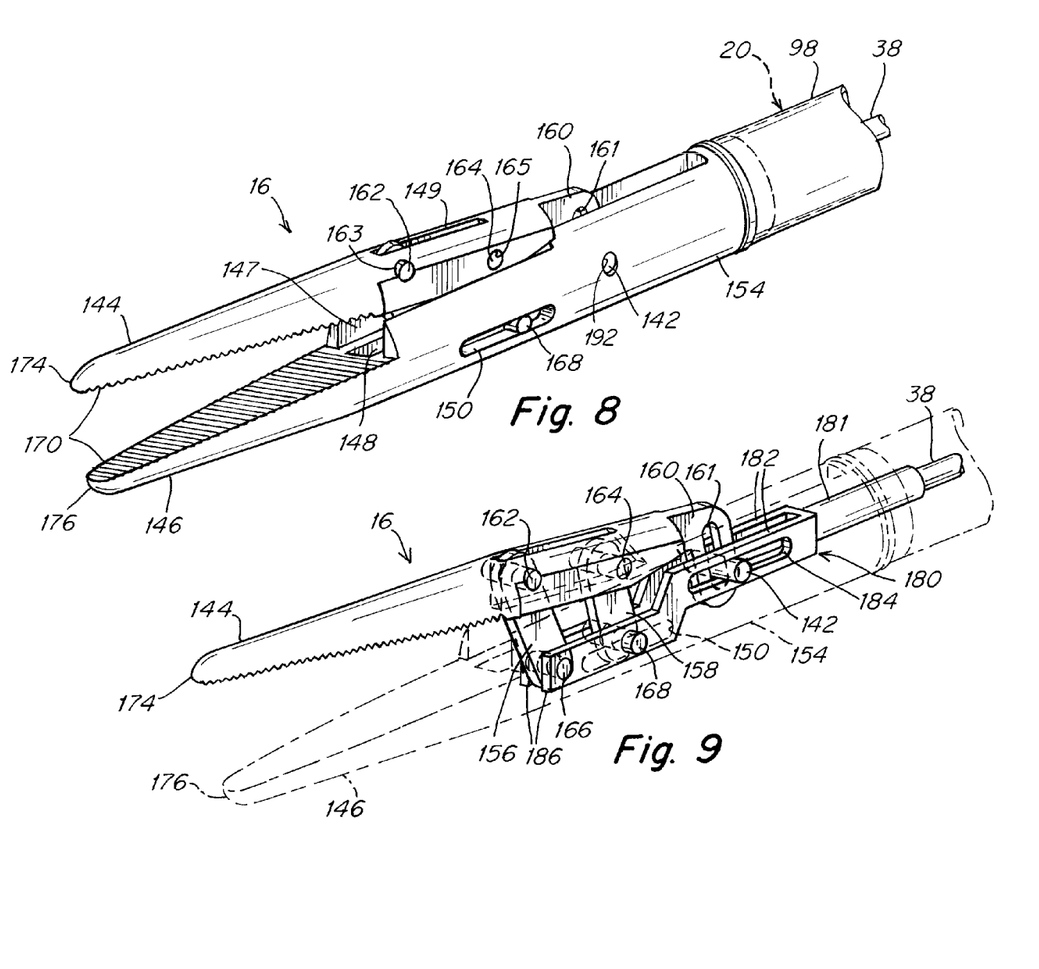
FIG. 8 is an enlarged perspective view of the parallel jaws end effector of the present invention used on the instrument of FIG. 1.
FIG. 9 is an enlarged perspective view of the parallel jaws end effector of FIG. 8 but with some portions shown in phantom for clarity.

The pin 142 is anchored in bores 192 and serves as a pivot location for the moveable jaw 144 thus controlling the distal travel of the moveable jaw to a relatively flat arc about pin 142 as indicated by the arrow 196. As illustrated in FIGS. 9 and 10 the upper ends of links 156, 158 extend into a slot 149 in the moveable jaw 144 and are joined by pivot pins 162, 164 to bores 163, 165 in the jaw 144. The lower ends of the links however, extend between the spaced apart lower arms 186 of yoke 180 and pivot pins 166, 168 join the lower ends of the respective links 156, 158 to bores 188, 190. Tilt axis 157 is defined between pins 162 and 166, while tilt axis 159 is defined between pins 164 and 168. Pin 168 in this embodiment is longer than pin 166 so as to extend into and ride in the respective slots 150 in the main body 154 of fixed jaw 154. The slots 150 are provided on opposite sides of the channel 147. This interlocking between the links and jaws provides a support guide to the yoke 180 as pressure is applied to the moveable jaw 144 as the yoke is slid distally and the jaw closes upon an object.

Pivot pin 142 also passes through slots 184 in upper arms 182 of yoke 180 and is force fit in bores 192 in the sides of main body 154 of the fixed jaw 146. This anchors the pivot pin 142 to the fixed jaw 146, and provides a pivot location for the moveable jaw, while further providing a support guide for the yoke 180. The slot 161 of extension arm 160 is elongated allowing the pin 142 to transition along the slot 161 as the slide member moves linearly as the jaws move to a closed position. Note the transition of the pin 142 in slot 161 from FIG. 11 to FIG. 14 where the jaws are fully closed. This translation occurs while maintaining the jaws in a parallel relationship with little or no lateral movement. The yoke 180 has a tubular guide or boss 181 which rides in bore 155 in the main body 154 of the fixed jaw 146. The boss 181 is firmly fixed on the end of cable 38 and is free to slide proximally/distally in the bore 155.

Figure 11:
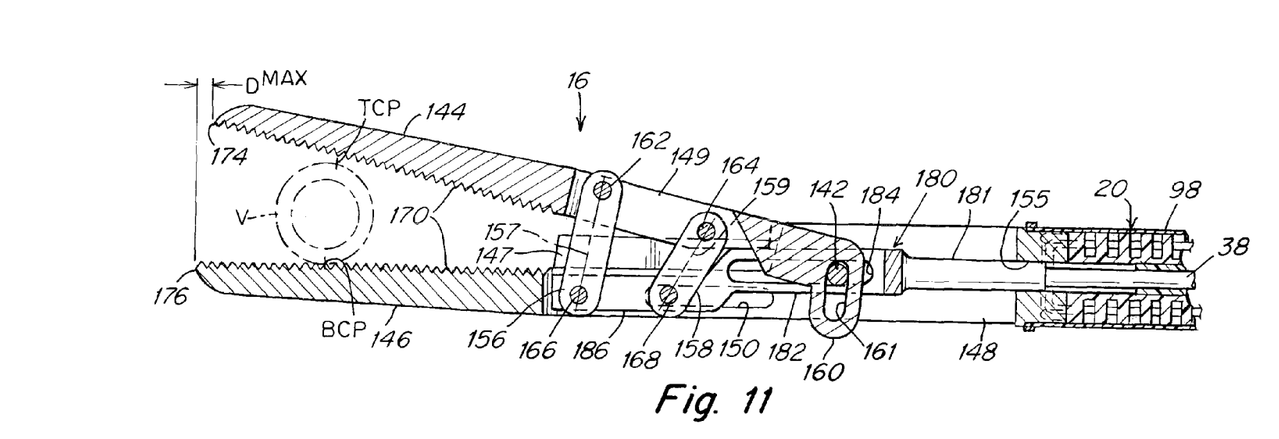
FIGS. 11-14 are schematic cross-sectional views of the parallel jaws end effector of the present invention in a sequence of positions from fully open to completely closed.
Figure 13:
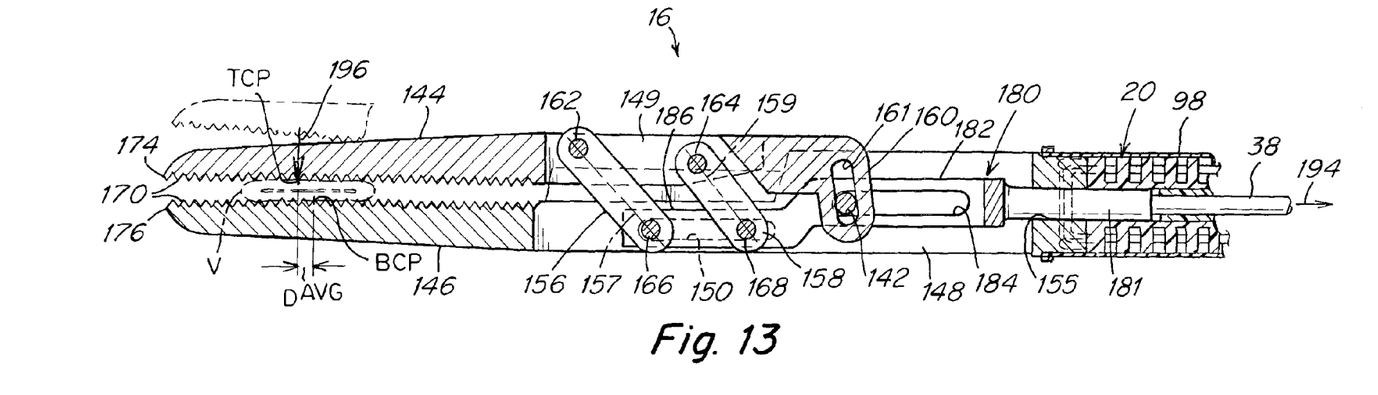
Figure 14:
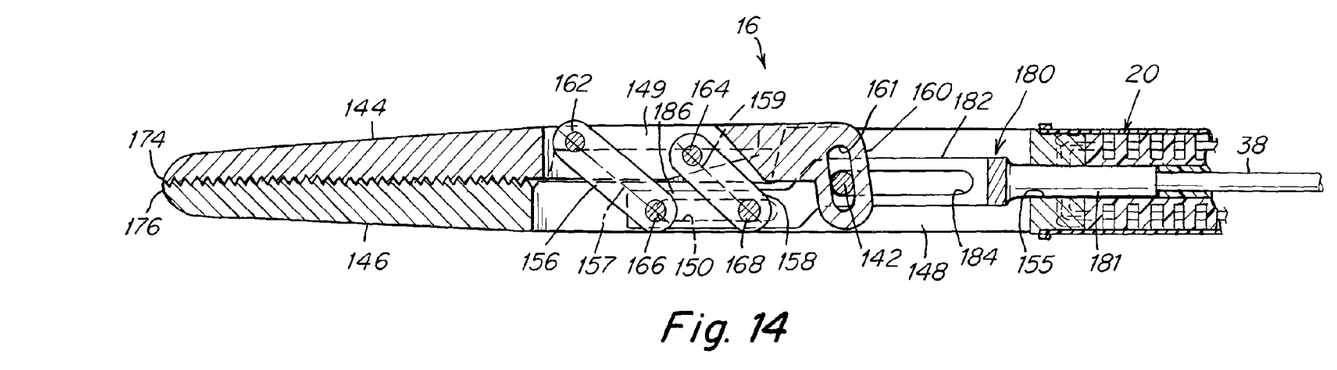

FIGS. 11-13 show a sequence of action as the jaws clamp down on an object such as a vein V. FIG. 11 shows the moveable jaw 144 in a full open position about to close down on vein V. In this position the tip 174 of the jaw 144 is situated a maximum distance DMAX proximally from the tip 176 of the fixed jaw 146. As the jaw activation lever 22 of instrument 10 (FIG. 1) is squeezed, the cable 38 is urged proximally (arrow 194) and the serrations 170 on jaw 144 make contact with top contact point TCP on vein V. as this occurs, the serrations 170 on jaw 146 make contact with bottom contact point BCP on vein V as shown in FIG. 12, squeezing down on the vein V. As the moveable jaw 144 closes down on the vein (arrow 196) very little rolling (lateral) action is imparted to the vein V as can be seen by the vector of the arrow 196. When the jaws have closed upon the vein V to the extent shown in FIG. 13 the TCP has traveled an average distance DAVG in relation to the point BCP. This greatly reduced rolling motion and practically eliminates any tearing action on soft tissue. FIG. 14 shows the jaws fully closed without any tissue present.

There are described herein two basic embodiments of the present invention. The first embodiment that has just been described employs a pulling action that does have the advantage of being able to impose a greater closing force. However, the principles of the present invention also apply to an end effector construction wherein a pushing action is used. This embodiment is now described in FIGS. 15-21.

Figure 17:
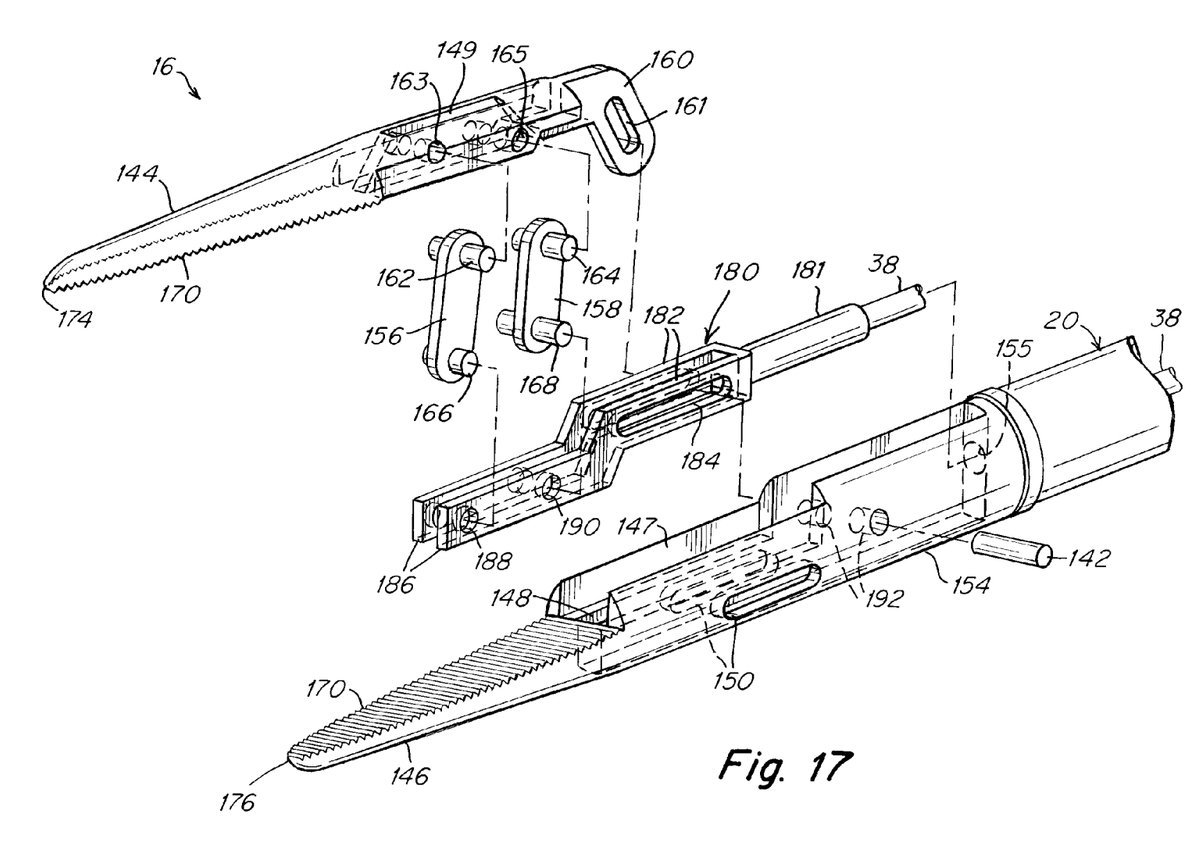
FIG. 17 is an exploded view of the end effector of FIG. 15.

In FIGS. 15-21 the same reference numbers are used, as previously identified in the instrument shown in FIGS. 8-14, such as the distal bendable member 20, the tool actuation cable 38, links 156, 158 and pivots 162, 164, 166 and 168. Instead of fixed pivot points for the lower ends of links 156, 158 the end effector construction of the present invention utilizes sliding pivot locations by means of the lower ends of the links 156, 158 being supported for translation by engagement with the yoke 180. The yoke 180 essentially functions as a slide member controlled from the actuation cable 38. The yoke 180 includes a boss 181 having extending therefrom elongated arms that each include upper arms 182 and lower arms 186 that are interconnected by an angled transition section. The pins 166, 168 are received in respective bores 188, 190 formed in the lower arms 186 of the yoke 180. As illustrated in FIG. 17, the arms 182 and 186 each include a pair of parallel spaced apart arms, with the lower arms 186 each have the respective aligned bores 188, 190.

Figure 18:
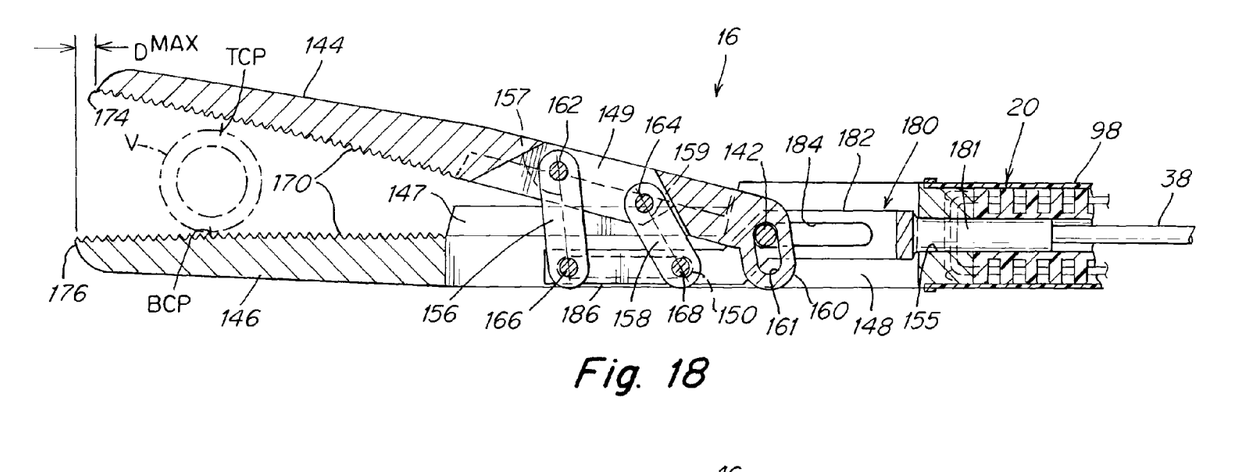
FIGS. 18-21 are schematic cross-sectional views of the parallel jaws end effector of FIGS. 15-17 in a sequence of positions from fully open to completely closed.
Figure 19:
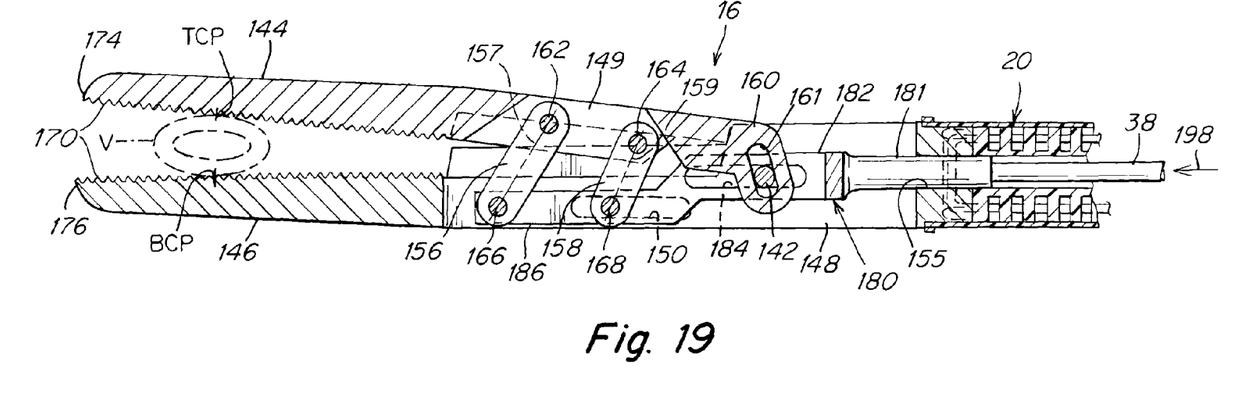
Figure 20:
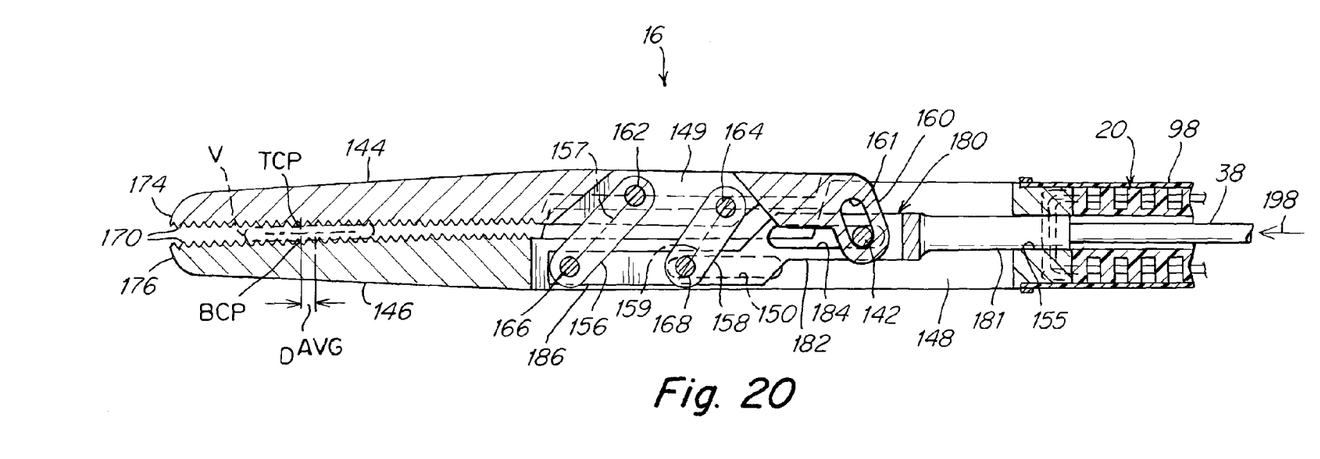

The yoke 180 travels distally when the cable 38 is pushed (arrow 198 in FIG. 19) to move the end effector jaws toward a closed position. This closing action involves having the pin 142 ride in the slot 161 of the extension arm 160 for controlling the action of the movable jaw 144. The extension 160 is somewhat elongated, as is the slot 161, and the extension 160 is integral with and extends substantially orthogonal to the length of the movable jaw 144 and the length of the upper arms 182 such as shown in FIG. 18. The action between the cable 38, yoke 180, pin 142 and movable jaw 144 causes a substantially parallel closing like that illustrated by the arrow 196 in FIG. 12. The result is that there is little or no lateral action between the respective jaws upon jaw closure.

Figures 15, 16:
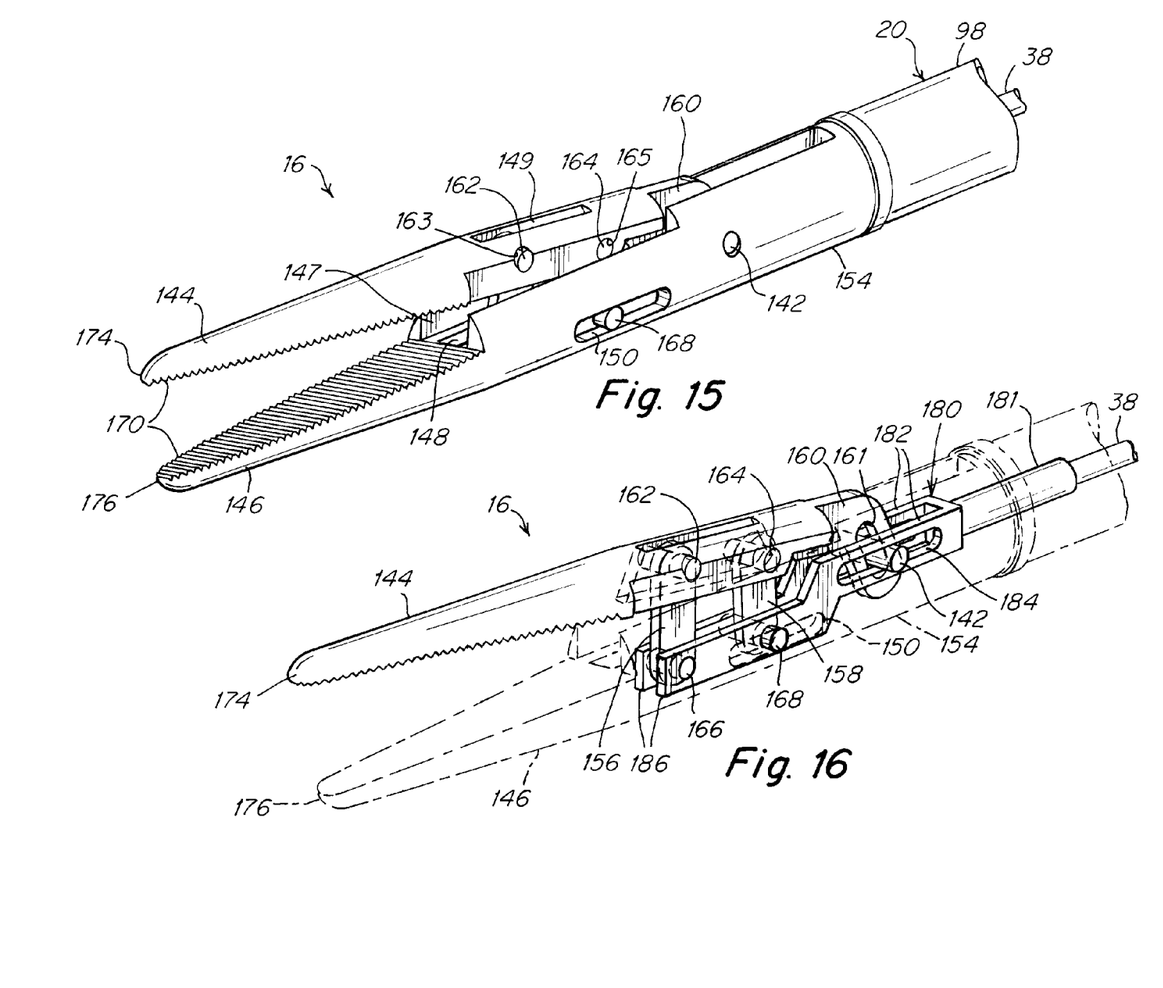
FIG. 15 is an enlarged perspective view of an alternate embodiment of the parallel jaws end effector of the present invention.
FIG. 16 is an enlarged perspective view of the parallel jaws end effector of FIG. 15 but with some portions shown in phantom for clarity.

The pin 142 is anchored in bores 192 and serves as a pivot location for the moveable jaw 144 thus controlling the distal travel of the moveable jaw to a relatively flat arc about pin 142 alike that indicated by the arrow 196 in FIG. 12. As illustrated in FIGS. 16 and 17 the upper ends of links 156, 158 extend into a slot 149 in the moveable jaw 144 and are joined by pivot pins 162, 164 to bores 163, 165 in the jaw 144. The lower ends of the links however, extend between the spaced apart lower arms 186 of yoke 180 and pivot pins 166, 168 join the lower ends of the respective links 156, 158 to bores 188, 190. Tilt axis 157 is defined between pins 162 and 166, while tilt axis 159 is defined between pins 164 and 168. Pin 168 is preferably longer than pin 166 so as to extend into and ride in the respective slots 150 in the main body 154 of fixed jaw 154. The slots 150 are provided on opposite sides of the channel 147. This interlocking between the links and jaws provides a support guide to the yoke 180 as pressure is applied to the moveable jaw 144 as the yoke is slid distally and the jaw closes upon an object.

Pivot pin 142 also passes through slots 184 in upper arms 182 of yoke 180 and is force fit in bores 192 in the sides of main body 154 of the fixed jaw 146. This anchors the pivot pin 142 to the fixed jaw 146, and provides a pivot location for the moveable jaw, while further providing a support guide for the yoke 180. The slot 161 is elongated allowing the pin 142 to transition along the slot 161 as the slide member moves linearly as the jaws move to a closed position. Note the transition of the pin 142 in slot 161 from FIG. 18 to FIG. 21 where the jaws are fully closed. This translation occurs while maintaining the jaws with little or no lateral movement. The yoke 180 has a tubular guide or boss 181 which rides in bore 155 in the main body 154 of the fixed jaw 146. The boss 181 is firmly fixed on the end of cable 38 and is free to slide proximally/distally in the bore 155.

Figure 21:
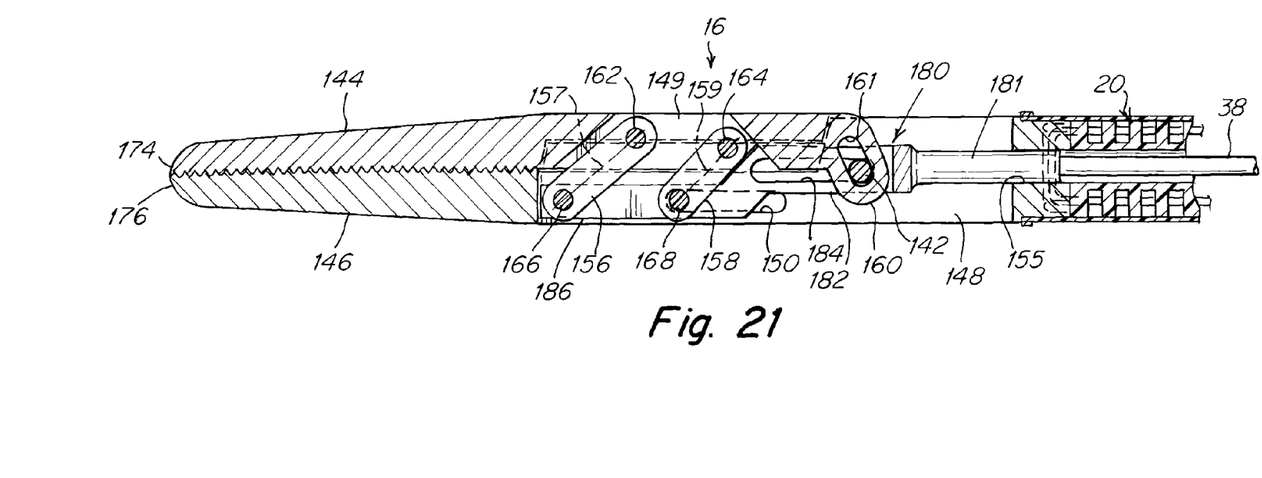

FIGS. 18-21 show a sequence of action as the jaws clamp down on an object such as a vein V. FIG. 18 shows the moveable jaw 144 in a full open position about to close down on vein V. In this position the tip 174 of the jaw 144 is situated a maximum distance DMAX proximally from the tip 176 of the fixed jaw 146. As the jaw activation lever 22 of instrument 10 (FIG. 1) is squeezed, the cable 38 is urged distally (arrow 198) and the serrations 170 on jaw 144 make contact with top contact point TCP on vein V. As this occurs, the serrations 170 on jaw 146 make contact with bottom contact point BCP on vein V like that shown in FIG. 12, squeezing down on the vein V. As the moveable jaw 144 closes down on the vein very little rolling (lateral) action is imparted to the vein V. When the jaws have closed upon the vein V to the extent shown in FIG. 20 the TCP will have traveled an average distance DAVG in relation to the point BCP. This greatly reduced rolling motion and practically eliminates any tearing action on soft tissue. FIG. 21 shows the jaws fully closed without any tissue present.

As can be seen in the sequential views of FIGS. 18-21, the axes 157, 159 respectively of links 156, 158 shift along with the lower pivot points (bores 188, 190) from a more proximal position (jaws open) relative to upper pivot points (pins 162, 164) to more distal position (jaws closed) relative to the upper pivot points (pins 162, 164) as the cable 38 is pushed distally. To state this in another way, and in connection with the sequential views of FIGS. 18-21, as the jaws move from an open position to a closed position, the axes 157, 159 tilt from a left position relative to the pins 166, 168, to a right position relative to the pins 166, 168. This is the reverse action of the pull version of the instrument illustrated FIGS. 11-14. In FIGS. 11-14, the axes 157, 159 respectively of links 156, 158 shift along with the lower pivot points (bores 188, 190) from a more distal position (jaws open) relative to upper pivot points (pins 162,164) to more proximal position (jaws closed) relative to the upper pivot points (pins 162, 164) as the cable 38 is pulled distally. To state this in another way, and in connection with the sequential views of FIGS. 11-14, as the jaws move from an open position to a closed position, the axes 157, 159 tilt from a right position relative to the pins 166, 168, to a left position relative to the pins 166, 168.

Having now described embodiments of the present invention, it should now be apparent to one skilled in the art that there are numerous other embodiments, and modifications thereof, that are anticipated as falling within the scope of the present invention. For example, the end effector construction described herein has been explained as associated with a pistol grip instrument. However, the end effector construction may also be used with a variety of other instrument constructions including, but not limited to, straight instruments as well as articulating instruments. The particular end effector construction may also be used in surgical robotics, wherein there may be motorized control and/or tele-operated control. Another variation is that the profile of the motion can be readily changed by adjusting the lengths of the links 156, 158. Also, the locations of the pivot points for the links can be varied. For example, the pivot points (pins 162, 164, 166 and 168) may be adjusted so that the tip of the jaws close first, or slightly before the remainder of the jaw surfaces 170 fully close. In the drawings the slot 161 is illustrated as straight. However, the slot 161 can also have other configurations such as an arcuate shape. The previous description references the grasping of a vessel, but the end effector can also be used in an application of vessel sealing, or other surgical procedure applications.

What is claimed is:

1. A medical instrument tool or end effector that has a longitudinal axis and that is comprised of:
    a fixed jaw having a distal grasping end and a proximal body end;
    a movable jaw having a distal grasping end and a proximal body end that includes an elongated slot;
    a slide member controlled from a tool actuator, adapted for linear translation and supported between the jaws;
    a pair of links that inter-couple between the slide member and the movable jaw;
    each link having opposed end support pins constructed and arranged to have the links disposed in a parallel and spaced apart relationship when the jaws are in a closed position;
    and a pivot member mounted at the fixed jaw and for engagement with the elongated slot in the body end of the movable jaw.

2. The medical instrument of claim 1 wherein the slide member also has an elongated slot, and the pivot member comprises a pivot pin that extends through the elongated slot in the slide member and into the elongated slot in the proximal body end of the movable jaw.

3. The medical instrument of claim 2 wherein the opposed end support pins include a top pin set and a bottom pin set, the top pin set pivotally mounted in the movable jaw, and the bottom pin set is pivotally mounted at the slide member.

4. The medical instrument of claim 1 wherein the opposed end support pins include a top pin set and a bottom pin set, the fixed jaw has an elongated slot, and one of the pins of the bottom pin set is received in the elongated slot of the fixed jaw.

5. The medical instrument of claim 1 wherein the movable jaw includes an extension that extends substantially orthogonal to the longitudinal axis, and the elongated slot at the proximal body end of the movable jaw is disposed along the extension.

6. The medical instrument of claim 1 wherein the slide member comprises a yoke including a body end connected with a tool actuation cable and a pair of spaced apart arms.

7. The medical instrument of claim 6 wherein said pair of arms include a set of upper arms and a contiguous set of lower arms.

8. The medical instrument of claim 1 wherein the slide member transitions proximally for closing the jaws.

9. The medical instrument of claim 1 wherein the slide member transitions distally for closing the jaws.

10. A medical instrument tool or end effector that is comprised of:
    a fixed jaw having a distal grasping end and a proximal body end;
    a movable jaw having a distal grasping end and a proximal body end;
    a slide member controlled from a tool actuator, adapted for linear translation and supported between the jaws;
    at least one link that inter-couples between the slide member and the movable jaw;
    and a pivot member mounted at the fixed jaw and for engagement with a slot in the body end of the movable jaw;
    wherein the slide member comprises a yoke including, a body end connected with a tool actuation cable and a pair of spaced apart arms;
    wherein said pair of arms include a set of upper arms and a contiguous set of lower arms;
and an angled transition section between sets of upper and lower arms.

11. The medical instrument of claim 10 wherein said at least one link comprises a pair of links each having top and bottom ends, and the lower arms each include bores for receiving respective pins that support the bottom ends of the links.

12. The medical instrument of claim 11 wherein the pivot member comprises a pivot pin and the upper arms include an elongated slot for receiving the pivot pin.

13. The medical instrument of claim 12 wherein the fixed jaw has an elongated slot for receiving one of the respective pins.

14. A medical instrument tool or end effector that has a longitudinal axis and that is comprised of:
    a first jaw having a distal grasping end, a proximal body end and a slot that extends in the direction of the longitudinal axis;
    a second jaw having a distal grasping end and a proximal body end;
    a slide member controlled from a tool actuator, adapted for linear translation and supported between the jaws, and including a slot;
    at least one link that inter-couples between the slide member and the second jaw;
    and a pivot member mounted at the first jaw and for engagement through the slot in the slide member to the second jaw;
    said at least one link having a lower pivot pin that is constructed and arranged to engage with the slide member and extend into the slot in the first jaw.

15. The medical instrument of claim 14 wherein the pivot member comprises a pivot pin and the proximal body end of the second jaw has an extension including an elongated slot that extends substantially transverse to the longitudinal axis and receives the pivot pin, and wherein said slot in said slide member extends in the longitudinal axis direction.

16. The medical instrument of claim 14 wherein said at least one link comprises a pair of links that inter-couple between the slide member and the second jaw, each link having opposed end support pins constructed and arranged to have the links disposed in a parallel and spaced apart relationship when the jaws are in a closed position, a lower one of said opposed end support pins comprising said lower pivot pin and pivotally engaged with the slide member.

17. The medical instrument of claim 16 wherein the bottom ends of the links are supported between the pair of spaced apart arms.

18. The medical instrument of claim 17 wherein the slide member comprises a yoke including a body end connected with a tool actuation cable and a pair of spaced apart arms.

19. The medical instrument of claim 18 wherein the bottom ends of the links are supported between the pair of spaced apart arms.

20. The medical instrument of claim 14 wherein the slide member transitions either proximally or distally for closing the jaws.

21. A medical instrument tool or end effector that has a longitudinal axis and that is comprised of:
    a fixed jaw having a distal grasping end, a proximal body end;
    a movable jaw having a distal grasping end a proximal body end and a slot;
    a slide member controlled from a tool actuator, adapted for linear translation and supported between the jaws;
    at least two links that inter-couple between the slide member and the movable jaw;
    and a pin member for engagement through the slot in the movable jaw;
    said at least two links having lower pivot pins that are constructed and arranged to engage with the slide member.

22. The medical instrument of claim 21 wherein the fixed jaw also has a slot, the pin member is mounted at the fixed jaw, one of the lower pivot pins extends into the slot in the fixed jaw, and the links are disposed in a parallel and spaced apart relationship to each other when the jaws are in a closed position.

* * * * *